US008374891B2

(12) United States Patent
Lassetter et al.

(10) Patent No.: US 8,374,891 B2
(45) Date of Patent: Feb. 12, 2013

(54) RECORD LOCATOR SERVICE

(75) Inventors: James K. Lassetter, Scottsdale, AZ (US); David M. Coyle, Sandy, UT (US); Jad G. Startin, Lehi, UT (US); Mohammed Pervaiz Ansari, Salt Lake City, UT (US); Mark B. Parker, West Jordan, UT (US); Carol L. Owen, Sandy, UT (US); Ashish V. Shah, Chicago, IL (US); Jared B. Crapo, Sandy, UT (US)

(73) Assignee: Medicity, Inc., Salt Lake City, UT (US)

( * ) Notice: Subject to any disclaimer, the term of this patent is extended or adjusted under 35 U.S.C. 154(b) by 409 days.

(21) Appl. No.: 12/263,960

(22) Filed: Nov. 3, 2008

(65) Prior Publication Data

US 2009/0150185 A1 Jun. 11, 2009

Related U.S. Application Data

(60) Provisional application No. 60/984,697, filed on Nov. 1, 2007.

(51) Int. Cl.
*G06F 19/00* (2011.01)
(52) U.S. Cl. ............................................................ 705/3
(58) Field of Classification Search .................. 705/2, 3; 707/104.1
See application file for complete search history.

(56) References Cited

U.S. PATENT DOCUMENTS

| 6,449,621 | B1* | 9/2002 | Pettovello | 1/1 |
| 2001/0041991 | A1* | 11/2001 | Segal et al. | 705/3 |
| 2002/0004727 | A1* | 1/2002 | Knaus et al. | 705/3 |
| 2003/0046114 | A1* | 3/2003 | Davies et al. | 705/3 |
| 2004/0249677 | A1* | 12/2004 | Datta et al. | 705/3 |
| 2006/0026043 | A1* | 2/2006 | Schneider et al. | 705/3 |
| 2007/0027715 | A1 | 2/2007 | Gropper et al. | |
| 2007/0027722 | A1 | 2/2007 | Hasan et al. | |
| 2007/0033066 | A1* | 2/2007 | Ammer et al. | 705/2 |

OTHER PUBLICATIONS

PCT International Search Report and Written Opinion, PCT Application No. PCT/US08/82276, Jan. 6, 2009, 8 pages.

* cited by examiner

*Primary Examiner* — John Pauls
(74) *Attorney, Agent, or Firm* — Patent Law Works LLP

(57) ABSTRACT

A system and method for accessing health care data are disclosed. A data retrieval service module is coupled to a client device and to one or more data sources, such as medical data sources, a master patient index or additional data retrieval service modules. The data retrieval service module receives a data request from the client device and transmits the data request to the one or more data sources. The data retrieval service module then receives data associated with the data request from die one or more data sources and generates catalog by aggregating data from multiple data sources. The catalog is then transmitted from the data retrieval service module to the client device, allowing the client device to access data obtained from various data sources.

24 Claims, 4 Drawing Sheets

… (1) RECORD LOCATOR SERVICE

CROSS REFERENCE TO RELATED APPLICATIONS

This application claims the benefit, under 35 U.S.C. §119(e) of U.S. Provisional Application No. 60/984,697, filed Nov. 1, 2007, which is incorporated by reference in its entirety.

BACKGROUND

1. Field of Art

The present invention generally relates to the field of medical information, and more specifically, to accessing medical records.

2. Description of the Related Art

Providing quality health care and related services (e.g., pharmaceutical services, medical services) depends on having the ability to reliably access various types of records. In the case of patients, information regarding a particular patient may be needed by various different types of health care related entities. For example, any one of a hospital, a health care organization, a clinic, a clinical or hospital lab, an insurance company, or a pharmacy may need access to particular computerized patient information. Such information retrieval generally occurs by querying a database associated with the health care related entity performing the query. The database typically contains all or part of what is referred to as a "Master Patient Index" (MPI), which is a collection of patient information and identifiers. Particularly, an MPI is a collection of indexed patient records, where each record contains information about a particular patient. In practice, user and system-level applications submit known or believed patient information to the database, which then uses the MPI patient matching logic to match the incoming data with information stored in the database. If a match is found, the record (or pointer thereto) is returned to the querying entity. If the patient cannot be matched, the MPI creates a new patient record.

While a typical database is designed to work within or for a particular health care related entity, such as a particular hospital or a particular medical group, including among disparate information systems across the health care related entity, the increased mobility of individuals throughout the overall health care system and the constant evolution of health care makes retrieval of patient information by one or more different local, state, regional, or national health care related entities more common. However, accessing medical information stored in different health care related entities is complicated by the presence of political issues among entities, the lack of cooperation between competing entities and the storage of medical information in different formats by different health care related entities.

Because different health care related entities generally have different ways of configuring, storing, submitting, searching for, and handling medical information, such as patient information. For example, one health care related entity could have policies in place or be configured to enter all '1's in a social security field of a query when the social security number of a patient is unknown, whereas another health care related entity could have policies in place or be configured to enter '123-45-6789' for an unknown social security number. Thus, when configuring a centralized database, algorithm adjustments aimed to improve a matching accuracy for one health care related entity could come at the expense of reducing matching accuracy for another health care related entity or requiring multiple health care related entities to drastically reconfigure their data storage and/or retrieval methods. Accordingly, because of such a "win/loss" effect and the overhead of modifying existing medical information storage by health care related entities, otherwise offsets the potential benefits of using a centralized database.

Another way to "share" medical information between multiple health care related entities involves the use of an electronic data interchange (EDI). EDI allows entities to transfer data according to prescribed business standards. However, although EDI can be used to share certain medical information, EDI is not helpful for determining the identity of a patient based on incomplete or ambiguous information. In other words, EDI poorly supports, if at all, reliably matching queries with patient records.

SUMMARY

A system and method for accessing health care data includes a client device, one or more data retrieval service modules and one or more data sources. A data retrieval service module is coupled to the client device and to the one or more data sources, such as medical data sources or a master patient index via additional data retrieval service modules. The data retrieval service module receives a data request from the client device and accesses a routing module included in the data retrieval service module. The routing module includes data identifying one or more data sources and instructions for accessing the one or more data sources. Using data from the routing module, the data retrieval service module transmits the data request to the one or more data sources. In one embodiment, one or more data retrieval service modules are used to transmit the data request to the one or more data sources. The data retrieval service module then receives data associated with the data request from the one or more data sources and generates catalogs by aggregating data from multiple data sources. The list of catalogs are then transmitted from the data retrieval service module to the client device, allowing the client device to access data obtained from various data sources.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF DRAWINGS

The disclosed embodiments have other advantages and features which will be more readily apparent from the following detailed description and the appended claims, when taken in conjunction with the accompanying drawings, in which:

DETAILED DESCRIPTION

Figure 1:
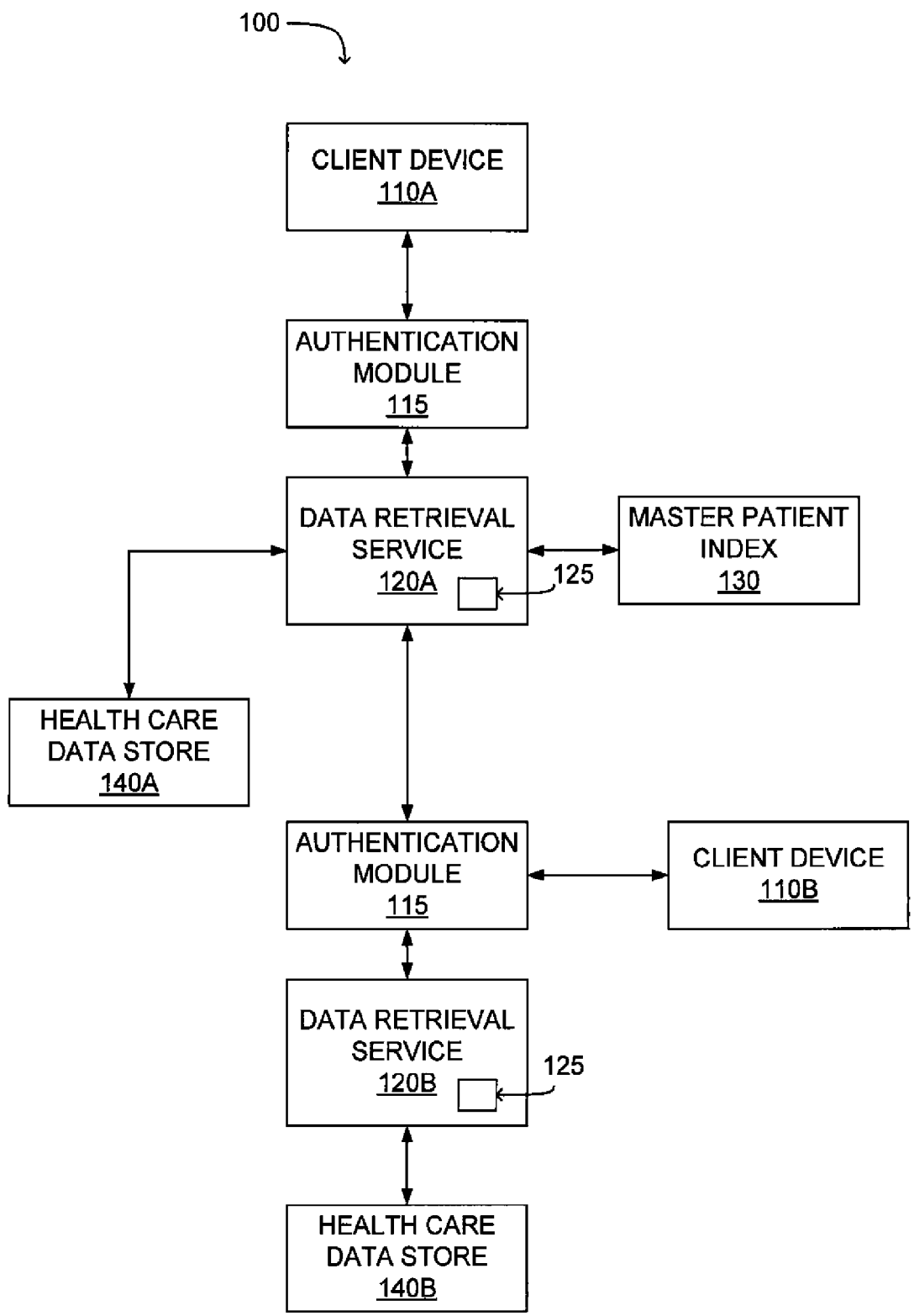
FIG. 1 is a block diagram of a system for retrieving medical data according to an embodiment of the present invention.

A system and method for retrieving medical data from one or more data sources is disclosed. For purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure or characteristic described in connection with the embodiment is included in at least one embodiment of the invention. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will be apparent from the description below. In addition, the present invention is not described with reference to any particular programming language. It will be appreciated that a variety of programming languages may be used to implement the teachings of the invention as described herein.

System Architecture

FIG. 1 is a block diagram of a system 100 for retrieving medical data according to an embodiment of the present invention. The system 100 comprises one or more client devices 110A, 110B, one or more authentication modules 115, one or more data retrieval service modules 120A, 120B and one or more health care data stores 140A, 140B which are communicatively coupled by a network, shown in FIG. 1 as various connecting lines between these components. In one embodiment, the system 100 also comprises a master patient index 130.

The client devices 110A, 110B are one or more computing devices having data processing and communication capabilities. Alternatively, the client devices 110A, 110B comprise one or more networks of computing devices, such as a computing network used by a hospital, clinic, medical insurance provider or other health care related entity. A client device 110A, 110B executes a health care application, such as the PROACCESS® application by Medicity or another application which receives information related to health care services and/or products provided to one or more patients.

The authentication module 115 is a computing device which receives a data request from a client device 110 and determines whether the data request from the client device 110 can be made. Hence, the authentication module 115 determines whether a data request is distributed to health care data stores 140A, 140B before the request is processed by a data retrieval service module and communicated to one or more health care data stores 140A, 140B. Hence, the authentication module regulates the types of data requests from a client device 110 that are permitted to access health care data stores 140A, 140B. For example, the authentication module 115 determines whether a data request from a client device 110 originates from a doctor or from a hospital administrator and grants or denies access to one or more health care data stores 140A, 140B accordingly, for example, by allowing a request from a doctor to be communicated to a health care data store 140 including laboratory test results while preventing a request from a hospital administrator to be communicated to the health care data store 140 including laboratory test results. The authentication module 115 determines access to health care data stores 140 by verifying the accuracy of a username and associated password received from a client device 110, by verifying a client device 110 has correctly supplied a valid token, such as a digital signature using their private half an asymmetric cryptographic key issued by a trusted authority, by applying lightweight directory access protocol (LDAP) methods to data received from the client device or other suitable methods of verifying the identity of the originator of a data request. In one embodiment, the authentication module 115 determines the role of the originator of a data request, such as determining whether the originator of a data request is a nurse, a physician, a hospital administrator or other health care related position, as well as the relationship between the originator of the data request and the data being requested, such as determining whether the originator of the data request is the primary physician of a patient identified by the data request.

The data retrieval service module 120 comprises a computing device which receives data requests from one or more client devices 110A, 110B and communicates the data requests to one or more health care data stores 140A, 140B. In an embodiment, a data retrieval service module 120A communicates data requests from one or more client devices 110A, 110B to an additional data retrieval service module 120B, allowing the additional data retrieval service module 120B to communicate the data requests to one or more health care data store 140A, 140B. The data retrieval service module 120 then receives data, such as patient identification data, patient demographic data, patient clinical data or other data associated with medical procedure or patient identification from one or more health care data stores 140A, 140B. In an embodiment, the data retrieval service uses an aggregation module 125 that then aggregates the data from the one or more health care data stores 140A, 140B to form a catalog of data that is communicated to the requesting client device 110A, 110B.

Hence, the data retrieval service module 120 allows one or more client devices 110A, 110B to retrieve medical data from one or more health care data stores 140A, 140B without directly communicating with the one or more health care data store 140A, 140B. This allows the client devices 110 to access disparate health care data store 140A, 140B that may reside in different physical locations. As shown in FIG. 1, one embodiment of a system 100 includes multiple data retrieval service modules 120A, 120B which communicate data between each other, allowing dissemination of a data request to a wider range of health care data stores 140.

To communicate data requests and data between client devices 110, health care data stores 140 and/or data retrieval service modules 120, one or more data retrieval service modules 120 include an aggregation module 125 which multiplexes data from health care data stores 140 or data retrieval service modules 120 to communicate the data from health care data stores 140 or data retrieval service modules 120 to a requesting client device 110. The aggregation module 125 is further described below in conjunction with FIG. 2.

Although described above as discrete modules, in various embodiments the authentication module 115 and the data retrieval service module 120 can be combined, allowing a single module to perform the functions of both the authentication module 115 and the data retrieval service module 120.

In one embodiment, the data retrieval service module is communicatively coupled to a master patient index 130 which includes a collection of patient information and identifiers. For example, the master patient index 130 is a collection of indexed patient records, where each record includes a patient identifier which uniquely identifies a patient and data associated with a patient identifier describing health care information associated with the patient identified by the patient identifier. In an embodiment, the master patient index 130 comprises a computing device, such as a server, desktop computer or laptop computer, including a database having one or more patient identifiers and data associated a patient identifier describing health care data, such as test results, demographic information, billing information, prescription history or similar data, associated with the patient identifier. In an alternative embodiment, the master patient index 130 includes a patient identifier and one or more pointers associated with the patient identifiers so that the pointers identify a data retrieval service module 120 that fulfills data requests and a health care data store 140 which includes health care data associated with the patient identifier, allowing the health care data to be retrieved from a health care data store 140 using the pointer to parameterize the data retrieval service module 120. Hence, the master patient index 130 matches data from the data retrieval service module 120 with one or more patients, allowing retrieval of health care data associated with a patient from the master patient index 130 or from a health care data store 140 identified by the master patient index 130. Although described above as discrete modules, in various embodiments the master patient index 130 and the data retrieval service module 120 can be combined, allowing a single module to perform the functions of both the master patient index 130 and the data retrieval service module 120.

One or more health care data stores 140A, 140B communicate with a data service retrieval module 120. A health care data store 140 comprises a computing device or other storage device including health care data, such as clinical results, prescription history, insurance or billing information, demographic information or other data associated with providing health care services or products to a patient. For example, a health care data store 140 comprises a clinical data catalog including clinical data, a medical insurance database including billing information for one or more patients, a record database including demographic information associated with one or more patients or other store of information applicable to health care services or products provided to one or more patients. Hence, a health care data store 140 includes health care data associated with one or more patients, allowing retrieval of data associated with a particular patient. In an embodiment, different health care data stores 140A, 140B store data in different formats and the data retrieval service module 120 reformats the received data using one or more data contracts into a format for use by a client device 110. This allows different health care data stores 140A, 140B to store data in different formats and also provide data to client devices in a standardized format generated by the data retrieval service module 120. Alternatively, one or more health care data stores 140A, 140B communicate data to a data retrieval service module 120 according to one or more contracts identifying a set of data from the health care data store 140 that is communicated to the data retrieval service module 120 and/or relationships data within the set of data that is communicated to the data retrieval service module 120.

In one embodiment, a network (shown generally as the lines connecting the components of FIG. 1) is used to transmit data or instructions between or among the client devices 110A, 110B, the authentication module 115, the data retrieval service modules 120A, 120B, the master patient index 130, the medical data stores 140A, 140B and/or other devices (not shown). The network may comprise a conventional wireless data communication system, for example, general packet radio service (GPRS), EEE 802.11 (or WiFi), IEEE 802.16 (or WiMax), Bluetooth, or any other suitable wireless communication system. Alternatively, the network may comprise a conventional wired data communication system, such as Ethernet, digital subscriber line (DSL), integrated services digital network (ISDN), or any other suitable wired communication system. In an embodiment, the network comprises a combination of a wireless communication system and a wired communication system. Alternatively, the network is replaced by a peer-to-peer configuration where one or more devices or modules directly communicate with each other.

Figure 2:
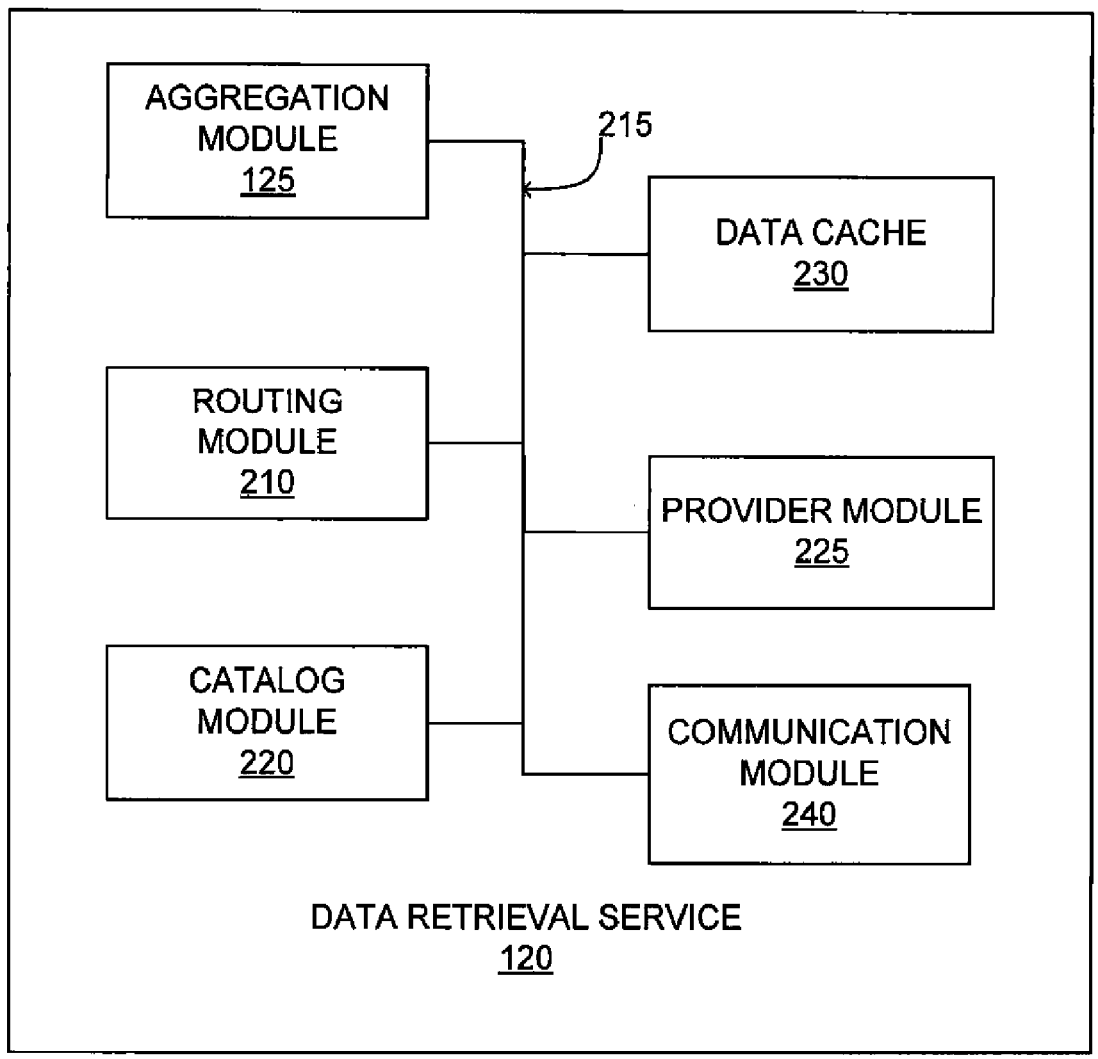
FIG. 2 is a block diagram a data retrieval service for retrieving medical data according to an embodiment of the present invention.

FIG. 2 is a block diagram a data retrieval service module 120 for retrieving medical data in more detail according to an embodiment of the present invention. In one embodiment, the data retrieval service module 120 comprises an aggregation module 125, a routing module 210, a catalog module 220, a data cache 230 and a communication module 240 which are coupled by a bus 215. Those of skill in the art will recognize that different embodiments can provide the functionality of FIG. 2 in different ways. Moreover, other embodiments can include different and/or additional features and/or components than the ones described here.

The aggregation module 125 receives, through the bus 215, data from one or more health care data sources 140 and/or the master patient index 130 received by the communication module 240 and combines the received data to form a data catalog. This allows the aggregation module 125 to organize data from different sources, such as different health care data stores 140 and/or the master patient index 130, into a single result set, or catalog, allowing data from disparate sources to be organized into a single result set, simplifying communication of data from a data retrieval service module 120 to a client device 110. In one embodiment, the aggregation module 125 communicates with the catalog module 220, which is further described below, to determine how to combine the received data into a data catalog or other result set. For example, the aggregation module 125 unions data received from one or more health care data stores 140 and/or the master patient index 130 into a single result set. As another example, the aggregation module 125 groups received data according to one or more rules from the catalog module 220. Hence, the aggregation module 125 allows data from various sources to be organized together to simplify communication of data to the client device 110 using the aggregated data rather than separately retrieving data from various health care data stores 140 and/or the master patient index 130.

The routing module 210 receives data requests, via the bus 215, from a client device 110 received by the communication module 240 and routes the received data requests to one or more health care data store 140 or one or more additional data retrieval service modules 120. In one embodiment, the routing module 210 includes a data source identifier which uniquely identifies the health care data stores 140, the master patient index 130 or data retrieval service modules 120 coupled to the data retrieval service module 120 including the routing module 210. An address and/or access instructions are associated with the data source identifier to describe how to access the health care data store 140 or routing module 210 associated with the data source identifier. Hence, the routing table 210 identifies one or more sources of data coupled to the data retrieval service module 120 and describes how to access the one or more sources of data. This allows the routing module 210 to communicate data requests to health care data stores 140 and/or the mater patient index 130 to retrieve the requested data.

In an embodiment, the routing module 210 initially determines a topology describing the relationship between the data retrieval service module 120 and one or more data sources, such as health care data stores 140, the master patient index 130 and data retrieval service modules 120, allowing the routing module 120 to identify data sources accessible by the data retrieval service module 120. This allows the routing module 210 to identify data sources from which to receive data. In an embodiment, the routing module 210 includes identifiers and access information for health care data stores 140 and/or data retrieval service modules 120 that directly communicate with the data retrieval service module 120. For example, a routing module 210 included in the data retrieval service module 120A includes identifiers and access information for the medical data store 140A, the master patient index 130 and the data retrieval service 120B so that the data retrieval service module 120A communicates data requests to the devices associated with the included identifiers. In one embodiment, the routing module 210 updates the identifiers and access information via delegation requests to the data sources, such as a health care data store 140, the master patient index 130, or other data retrieval service modules 120 coupled to the data retrieval service module 120 including the routing module 210.

The catalog module 220 includes one or more rules describing how to group data received from one or more health care data stores 140, the master patient index 130 and/or other data sources. Hence, the catalog module 220 allows the aggregation module 125 to generate one or more catalogs, which are collections of related data having a common entity, from the received data. For example, the catalog module 220 includes rules for organizing received data having a common patient or patient identifier, rules for organizing data having the same type, rules for organizing data originating from the same type of clinical encounter or other suitable data. In one embodiment, the catalog module 220 identifies the one or more criteria for grouping data together as well as one or more relationships between criteria for grouping data, allowing the data retrieval service module 120 to link data originating from disparate sources. The catalog module 220 generates one or more collections of related data having a common logical entity, such as a patient, an encounter, a laboratory result or other type of clinical data. A generated catalog includes multiple representations of the data as well as unique data identifiers associated with the data source from which the data was received which allow data requests to be parameterized.

In one embodiment, the data retrieval service module 120 also includes a provider module 225 which translates data received from one or more data sources into a format defined by the data retrieval service module 120. The provider module 225 includes data describing the format in which different data sources store and communicate data, as well as one or more data contracts which identify a set of data from the data source used by the data retrieval service module 120 and/or relationships data within the identified set of data that received by the data retrieval service module 120. Hence, the provider module 225 allows the data retrieval service module 120 to receive data in different formats and convert the received data into a standardized format defined by a data contract. This allows data sources to store data in a format different than the format used by the client device 110 requesting data by having the provider module 225 reformat data from data sources into a format usable by the client device 110.

The aggregation module 125, routing module 210, the catalog module 220 and the provider module 225 can be implemented in many ways. For example, they can be one or more software processes executable by a processor (not shown) and/or a firmware application. The software and/or firmware can be configured to operate on a general purpose microprocessor or controller, a field programmable gate array (FPGA), an application specific integrated circuit (ASIC) or a combination thereof.

In one embodiment, the data retrieval service module 120 includes a data cache 230, which comprises a persistent storage device, such as a hard disk drive or flash memory device, a non-persistent storage device, such as dynamic random access memory (DRAM), static random access memory (SRAM) or other device storing data for at least a limited time or a combination of a persistent storage device and a non-persistent storage device. The data cache 230 stores one or more filters that are applied to a data set or catalog to return a subset of the dataset or catalog or stores a subset of a catalog or dataset previously generated by application of one or more filters to the catalog or dataset. Hence, the data cache 230 allows the data retrieval service module 120 to store the results of frequently received data requests or to store a set of common data requests to reduce the time needed to return requested data to a client device 110. In an embodiment, the data cache 230 is periodically updated or is updated as data requests are received from a client device, allowing the data cache 230 to include the most relevant filters or results of filtering.

The data retrieval service module 120 further comprises a communication module 240 enabling the data retrieval service module 120 to communicate with a client device 110, one or more health care data stores 140, the master patent index 130 and/or one or more additional data retrieval service modules 120 or other devices. In an embodiment, the communication module 240 comprises a transceiver such as for infrared communication, Bluetooth communication, 3G communication, radio frequency communication, or any other wireless communication technique. In an alternative embodiment, the communication module 240 comprises a conventional wired connection, such as Ethernet, Universal Serial Bus (USB), or other wired communication techniques. Alternatively, the communication module 240 comprises both a wired connection and a transceiver. The communication module 240 allows data, commands and/or information to be distributed using network protocols, such as Transmission Control Protocol (TCP), Internet Protocol (IP), Hypertext Transmission Protocol (HTTP), or other protocols capable of communicating data or information.

System Operation

Figure 3:
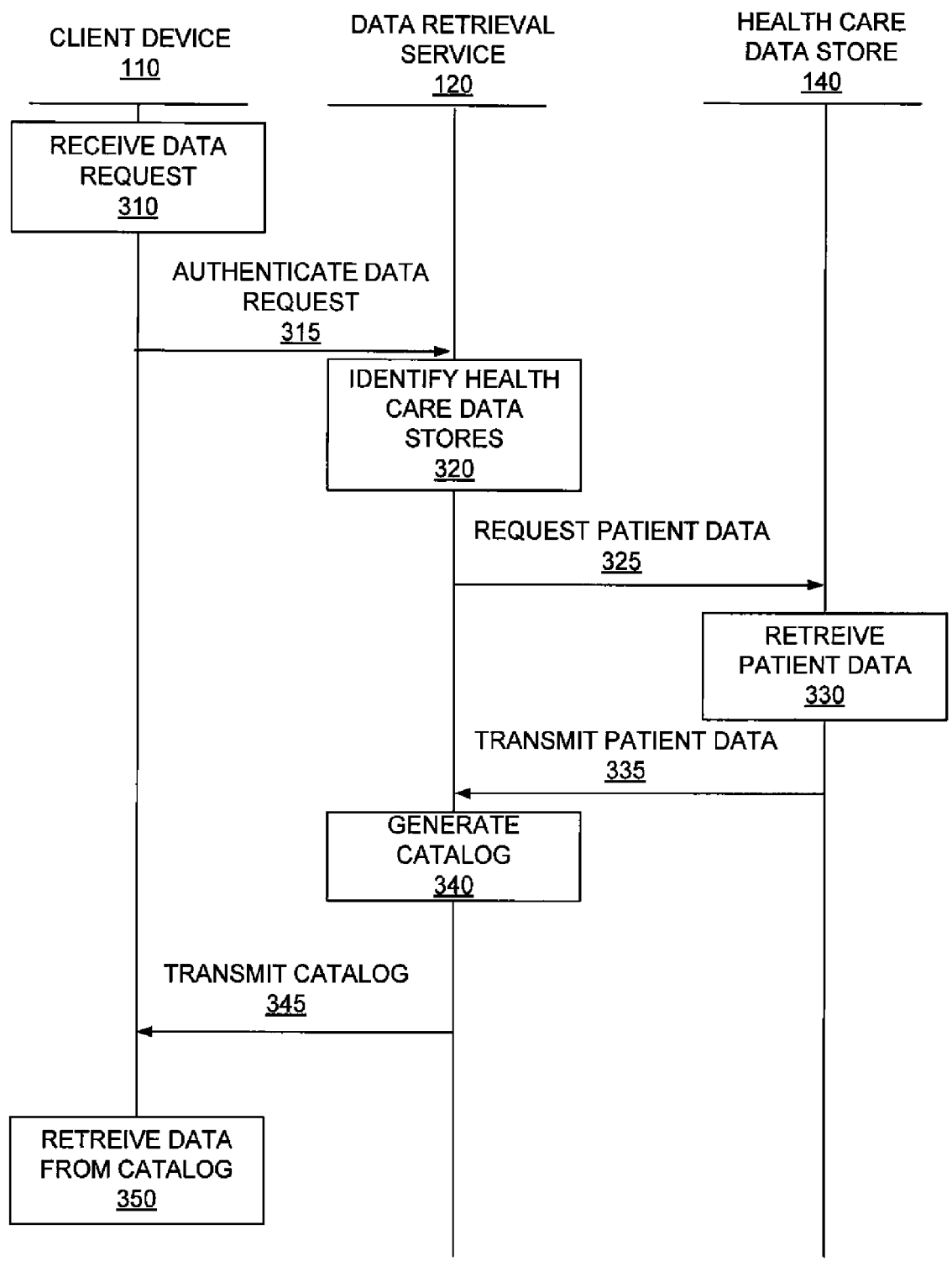
FIG. 3 is an event diagram of a method for retrieving medical data according to an embodiment of the present invention.

FIG. 3 is an event diagram of a method for retrieving medical data according to an embodiment of the present invention. For purposes of illustration, FIG. 3 depicts interaction between a client device 110, a data retrieval service module 120 and a medical data store 140. However, in other embodiments, multiple data retrieval service modules 120 and multiple health care data stores 140 communicate with each other in addition to communicating with the client device.

Initially, the client device 110 receives 310 a data request from a user. In one embodiment, a user accesses a health care application operating on the client device 110 and requests data associated with health care products or services. For example, a user requests to view clinical data, such as medical diagnoses or laboratory test results, from the client device 110. The data request includes one or more filters identifying the data to be retrieved. For example, the data request includes one or more filters, such as age, gender or other criteria which describe a set of patients. For example, the filters included in the data request uniquely identify a single patient or identify a subset of closely matched patients from which an individual patient is later selected.

The data request is then authenticated 315 by a data retrieval service module 120 to verify that the user generating the data request is permitted to access the requested data. For example, the data request includes a session security token which is authenticated by the data retrieval service 120. To authenticate 325 a data request, the data retrieval service module 120 verifies that the session security token included in the data request is generated by an authority, such as a client device 110, trusted by the data retrieval service module 120. As another example, to authenticate 315 the data request, the data retrieval service 120 determines the role of the user generating the data request in providing health care products or services and determines the relationship of the user generating the data request to the requested data. In another embodiment, an authentication module 115 authenticates 315 the data request and then transmits the data request to a data retrieval service module 120 if the user associated with the data request is authenticated 315. Authentication 315 also identifies any data that the requesting user is not permitted to access so that only data sources which the requesting user is permitted to access are used to provide the requested data. In an embodiment, if the data request is not authentication 315, an error message is returned to the client device 110 to indicate that the requested data was not retrieved.

If the data request is authenticated 315, the data retrieval service module 120 identifies 320 one or more health care data stores 320 coupled to the data retrieval service module 120 using the routing table 210 included in the data retrieval service module 120. The data retrieval service module 120 uses information from the routing table 210 identifying 210 one or more health care data stores 140, a master patient index 130 and/or additional data retrieval service modules 120 coupled to the data retrieval service 120, and how to access the one or more health care data stores 140, a master patient index 130 and/or additional data retrieval service modules 120 coupled to the data retrieval service 120 to request 325 data associated with one or more patients. For example, the data request which describes characteristics of one or more patients is transmitted from the data retrieval source module 120 to one or more health care data stores 140 using the information from the routing module 210. In an embodiment, the data request is also transmitted to a master patient index 130 and/or additional data retrieval service modules 120.

Upon receiving the data request, the health care data store 140 retrieves 330 patient data associated with one or more patients by applying the one or more filters included in the data request to the data stored in the health care data store 140. For example, if the data request includes filters identifying male patients born in 1963 with a residence address in Wyoming, the medical data store 140 retrieves 330 stored data associated with male patients born in 1963 having a residence address in Wyoming. The medical data store 140 then transmits 335 one or more pointers specifying one or more identifiers for accessing the requested data to the data retrieval service 120. The transmitted pointers describe how to access the requested data within the medical data store 140. In an embodiment, data is transmitted 335 in addition to the pointers, so that the data retrieval service module 120 receives a pointer describing the health care data store 140 and the data from the health care data store 140.

The data retrieval service module 120 then generates 340 a catalog including the pointers from the health care data store 140 using the aggregation module 125 and the catalog module 220. Hence, the data retrieval service module 120 generates 340 an aggregated result set, or catalog, describing how to retrieve data from one or more health care data stores 140. This allows the data retrieval service module 120 to maintain a catalog describing one or more health care data stores 140 including data associated with a data request and how to access data included in a health care data store 140. In an embodiment, the catalog also includes data from the health care data store 140 associated with the data request, so that the catalog includes the requested data and pointers describing the health care data store 140 where the data originated. The catalog is then transmitted 345 to the client device 110, providing the client device with an aggregated result set, or catalog, allowing a health care application included in the client device 110 to retrieve 350 data from the catalog.

Hence, the data retrieval system module 120 allows a client device 110 to access data from multiple health care data stores 140. Using the data retrieval module 120 to communicate data requests and data between one or more health care data stores 140 and one or more client devices 110 allows the number of health care data stores 140 in disparate locations to be accessed by a client device 110 and allows the number of health care data stores 140 to be dynamically modified without disrupting operation of the client device 110. Additionally, using the data retrieval service module 120 allows the client device 110 to receive data from a variety of health care data stores 140 which store data in different formats by using the data retrieval service module 120 to communicate data to the client device 110 in a standardized format.

Figure 4:
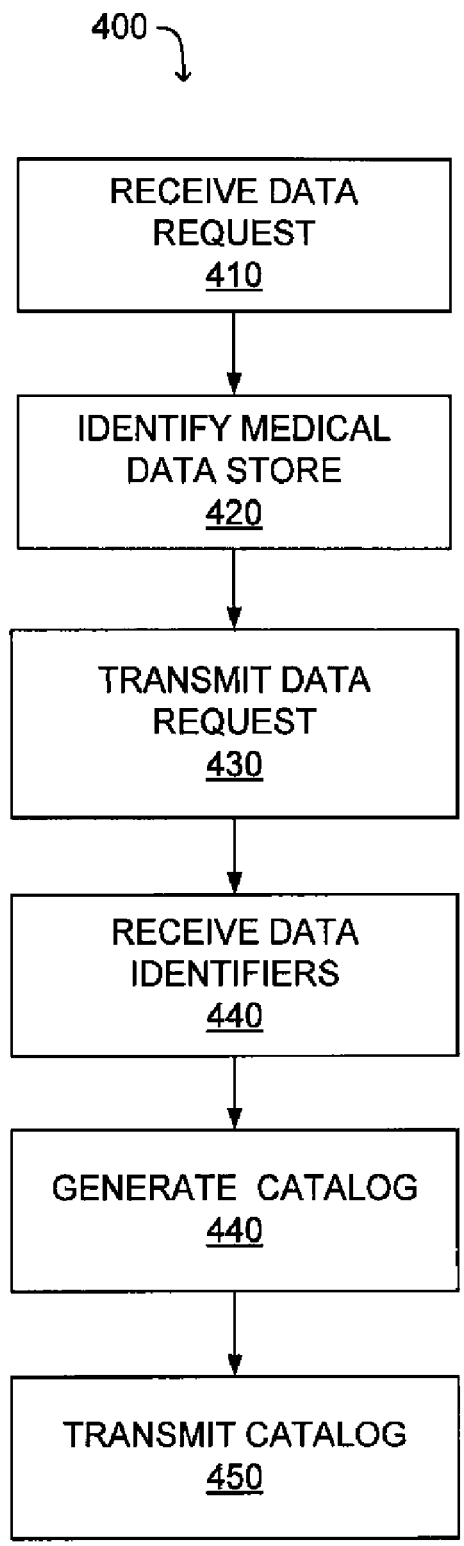
FIG. 4 is a flow chart of a method for retrieving medical data according to an embodiment of the present invention.

FIG. 4 is a flow chart of a method 400 for retrieving medical data according to an embodiment of the present invention. In an embodiment, the steps of the method 400 are implemented by a processor included in the data retrieval service module 120 executing software or firmware instructions that cause the described actions. Those of skill in the art will recognize that one or more of the methods may be implemented in embodiments of hardware and/or software or combinations thereof. For example, instructions for performing the described actions are embodied or stored within a computer readable medium. Furthermore, those of skill in the art will recognize that other embodiments can perform the steps of FIG. 4 in different orders. Moreover, other embodiments can include different and/or additional steps than the ones described here.

The data retrieval service module 120 receives 410 a data request from the client device 110 via the communication module 240. In one embodiment, the data request is associated with a user and/or client device and includes data identifying the user and/or client device. The data request includes one or more filters identifying the data to be retrieved. For example, the data request includes one or more filters, such as age, gender or other criteria which describe a set of patients. In one embodiment, the data retrieval service module 120 authenticates the data request to determine whether the user or client device 110 originating the data request is permitted to access the requested data. For example, the data retrieval service module 120 authenticates a username and password included in the data requestor determines whether the data request is received from a client device 110 includes a certificate. As another example, after receiving 410 the data request, the data retrieval service 120 determines the role of the user associated the data request in providing health care products or services (e.g., determines whether the user is a primary physician, a laboratory technician, a medical insurance company employee or other position associated with medical care) and determines the relationship of the user associated with the data request to the requested data.

The data retrieval service module 120 then identifies 420 one or more health care data stores 140 coupled to the data retrieval service module 120 by accessing the routing module 210. In one embodiment, the routing table 210 periodically determines data sources, such as health care data stores 140, a master patient index 130 and/or additional data retrieval service modules 120, coupled to the data retrieval service module 120 to maintain a current description of one or more data sources accessible by the data retrieval service module 120. As the routing module 210 identifies data sources and describes how the data retrieval service module 120 accesses the data sources, information from the routing module 210 is used to transmit 430 the data request to one or more data sources using the communication module 240. For example, the data request which describes characteristics of one or more patients is transmitted 240 to one or more health care data stores 140 using the information from the routing module 210. In an embodiment, the data request is also transmitted 430 to a master patient index 130 and/or additional data retrieval service modules 120.

The data locator service module 120 then receives 440 data identifiers from a health care data store 140, the master patient index 130, an additional data locator service module 120 or another data source responsive to the transmitted data request. In an embodiment, the received data identifier is patient data associated with one or more patients which is generated by a data source applying the one or more filters included in the data request to data that is locally stored by a data source. In an embodiment, the data includes one or more pointers which specify how to access the requested data from a data source, simplifying subsequent retrieval of the data from a data source by using a pointer. In an embodiment, data and pointers to the data are received 440, allowing the data retrieval service module 120 to identify both a pointer describing the data source including the data and the data from the data source.

A catalog including the pointers from the data source is then generated 440 using the aggregation module 125 and the catalog module 220. Hence, the data retrieval service module 120 generates 440 an aggregated result set, or catalog, describing how to retrieve data from one or more health care data stores 140 as well as identifying the data received form the data sources. The generated catalog allows the data retrieval service module 120 organize data from one or more data sources, simplifying subsequent use of the retrieved data. In one embodiment, the catalog includes the data associated with a data request and how to access data included in a data source. In an embodiment, the catalog also includes instructions for retrieving data from a data source, so that the catalog describes the location of the data and how to retrieve data, simplifying retrieval of data from a data source using the catalog. The catalog is then transmitted 350 to the client device 110 or user associated with the data request, providing the client device 110 with an aggregated result set, or catalog, including data from one or more data sources. This allows a health care application included in the client device 110 to access data from a variety of data sources using the received catalog.

The data retrieval service module 120 communicates received data requests to one or more data sources, such as health dare data sources 140, a master patient index 130 or additional data retrieval service modules 120, allowing various data sources to be examined for data associated with the data request, increasing the amount of data which is examined. Additionally, by communicating data and data requests between client devices 110 and data sources using the data retrieval service module 120, data sources can be dynamically added, removed or modified without affecting operation of the client devices 110.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats. Furthermore, as will be apparent to one of ordinary skill in the relevant art, the modules, routines, features, attributes, methodologies and other aspects of the present invention can be implemented as software, hardware, firmware or any combination of the three. Of course, wherever a component, an example of which is a module, of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

What is claimed is:

1. A system for accessing health care data comprising:
a computer processor;
an authentication module stored on a memory and executable by the computer processor, the authentication module configured to receive a data request from a user of a client device and authenticate the data request by determining a relationship between the user and data being requested and granting or denying access to the data based on the relationship, wherein the data request includes one or more filters describing one or more patients and responsive to the user being an administrator and the data request being for laboratory test results, the authentication module is configured to deny the administrator access to the data request; and
a first data retrieval service module coupled to the authentication module, to the client device and to a plurality of data sources that include health care data associated with the one or more patients, the first data retrieval service module configured to:
determine a topology describing a relationship between the first data retrieval service module and the plurality of data sources to determine access instructions for communicating the data request to the plurality of data sources,
update the access instructions by transmitting delegation requests to the plurality of data sources,
receive the data request from the authentication module and transmit the data request to a first set of data sources from the plurality of data sources,
receive health care data corresponding to the data request and pointers describing how to access the health care data within the first set of data sources from the first set of data sources,
generate a catalog from the received health care data and pointers received from the first set of data sources that is organized into a single result set,
reformat at least a portion of the catalog into a format for use by the client device based on the data request and transmit at least a portion of the reformatted catalog to the client device; and
a data cache coupled to the first data retrieval source module, the data cache configured to update a set of previously generated catalogs to include the reformatted catalog, wherein the set of previously generated catalogs reduces a time for returning the data being requested to the client device.

2. The system of claim 1, wherein the authentication module authenticates the data request by verifying that the client device supplied a valid token.

3. The system of claim 1, wherein the first data retrieval service module generates the catalog by applying one or more rules to the received health care data corresponding to the data request, the one or more rules describing one or more relationships between the received health care data corresponding to the data request.

4. The system of claim 1, wherein the one or more filters includes at least one of an age, a gender and a location describing the one or more patients.

5. The system of claim 1, wherein at least one of the plurality of data sources comprises a health care data store including data associated with health care products or services associated with the one or more patients.

6. The system of claim 1, wherein at least one of the plurality of data sources comprises a master patient index including a collection of indexed patient records, each patient record including a patient identifier uniquely identifying a patient from the one or more patients and health care data associated with the patient.

7. The system of claim 1, further comprising:
a second data retrieval service module, the second data retrieval service module coupled to a second set of data sources from the plurality of data sources.

8. The system of claim 1, wherein the authentication module receives the data request from the client device and determines whether the plurality of data sources are accessible by verifying the data request.

9. The system of claim 1, wherein the first data retrieval service module further determines whether the plurality of data sources are accessible by verifying the data request.

10. The system of claim 1, wherein the authentication module further transmits an error message to the client device in response to denying access to the data.

11. An apparatus for accessing health care data comprising:
a computer processor;
a routing module stored on a memory and executable by the computer processor, the routing module configured to identify a plurality of data sources, determine a topology describing a relationship with the plurality of data sources to determine access instructions for communicating a data request to the plurality of data sources, update the access instructions by transmitting delegation requests to the plurality of data sources and associate the data request with a first set of data sources from the plurality of data sources;
an authentication module stored on the memory and executable by the computer processor, the authentication module configured to receive the data request from a user of a client device and authenticate the data request by determining a relationship between the user and data being requested and granting or denying access to the data based on the relationship, wherein the data request includes one or more filters describing one or more patients and responsive to the user being an administrator and the data request being for laboratory test results, the authentication module denies the administrator access to the data request;
an aggregation module stored on the memory and executable by the computer processor, the aggregation module configured to receive health care data corresponding to the data request and pointers describing how to access the health care data from the first set of data sources and generate a catalog from the health care data and pointers received from the first set of data sources that is organized into a single result set;
a provider module stored on the memory and executable by the computer processor, the provider module configured to reformat at least a portion of the catalog into a format for use by the client device based on the data request;
a communication module stored on the memory and executable by the computer processor, the communication module coupled to the routing module and the aggregation module, the communication module configured to transmit the data request to the first set of data sources using the access instructions from the routing module, receive the health care data corresponding to the data request and pointers describing how to access the health care data within the first set of data sources from the first set of data sources and transmit at least a portion of the reformatted catalog to the client device; and
a data cache coupled to the aggregation module, the data cache configured to update a set of previously generated catalogs to include the reformatted catalog, wherein the set of previously generated catalogs reduces a time for returning the data being requested to the client device.

12. The apparatus of claim 11, further comprising:
a catalog module coupled to the aggregation module, the catalog module including one or more rules for associating the health care data received from the first set of data sources to generate the catalog.

13. The apparatus of claim 12, wherein the one or more rules include at least one of a common patient identifier and a common clinical encounter.

14. The apparatus of claim 11, wherein the authentication module further authenticates the data request by applying a lightweight directory access protocol.

15. The apparatus of claim 11, wherein one or more filters include at least one of an age, a gender and a location describing the one or more patients.

16. A method for accessing health care data comprising:
receiving, with a processor, a data request from a user of a client device, the data request including one or more filters describing a set of patients;
authenticating, with the processor, the data request by determining a relationship between the user and data being requested and granting or denying access to the data based on the relationship, wherein responsive to the user being an administrator and the data request being for laboratory test results, the authentication module denies the administrator access to the data request;
determining, with the processor, a topology describing a relationship with a plurality of data sources to determine access instructions for communicating the data request to the plurality of data sources,
updating, with the processor, the access instructions by transmitting delegation requests to the plurality of data sources,
identifying, with the processor, a first set of data sources from the plurality of data sources, the first set of data sources associated with the data request;
transmitting, with the processor, the data request to the first set of data sources associated with the data request;
receiving, with the processor, health care data and pointers describing how to access the health care data within the first set of data sources from the first set of data sources associated with the data request, the health care data associated with the set of patients described by the data request;
generating, with the processor, a catalog from the received health care data and pointers received from the first set of data sources that is organized into a single result set;
reformatting, with the processor, at least a portion of the catalog into a format for use by the client device based on the data request;
transmitting at least a portion of the reformatted catalog to the client device and
updating a set of previously generated catalogs to include the reformatted catalog, wherein the set of previously generated catalogs reduces a time for returning the data being requested to the client device.

17. The method of claim 16, further comprising:
authenticating the data request by verifying that the client device supplied a valid token.

18. The method of claim 16, wherein receiving the data request from the client device comprises:
verifying the data request to determine whether to restrict transmission of the data request to the first set of data sources.

19. The method of claim 16, wherein generating the catalog from the health care data received from the first set of data sources comprises:
applying one or more rules to the health care data received from the first set of data sources, the one or more rules associating the health care data from each of the first set of data sources.

20. The method of claim 19, wherein the one or more rules include at least one of a common patient identifier and a common clinical encounter.

21. The method of claim 16, wherein the health care data received from the first set of data sources associated with the data request includes an identifier associated with each of the first set of data sources providing the health care data.

22. The method of claim 16, wherein at least one of the first set of data sources comprises a health care data store including data associated with health care products or services associated with the set of patients.

23. The method of claim 16, wherein at least one of the first set of data sources comprises a master patient index including a collection of indexed patient records, each patient record including a patient identifier uniquely identifying a patient from the set of patients and health care data associated with the patient.

24. The method of claim 16, further comprising authenticating the data request by applying a lightweight directory access protocol.

* * * * *